US012648828B2

(12) United States Patent
Valster et al.

(10) Patent No.: US 12,648,828 B2
(45) Date of Patent: Jun. 9, 2026

(54) MEDICAL INTERVENTIONAL DEVICE HAVING OPTICAL TEMPERATURE OR PRESSURE SENSOR

(71) Applicant: KONINKLIJKE PHILIPS N.V., Eindhoven (NL)

(72) Inventors: Susanne Maaike Valster, Valkenswaard (NL); Ke Wang, Valkenswaard (NL); Cornelis Petrus Hendriks, Eindhoven (NL); Martinus Bernardus Van Der Mark, Best (NL); Emiel Peeters, Eindhoven (NL); Gert Wim 't Hooft, Eindhoven (NL); Franciscus Johannes Gerardus Hakkens, Eersel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 537 days.

(21) Appl. No.: 17/668,094

(22) Filed: Feb. 9, 2022

(65) Prior Publication Data

US 2022/0265382 A1      Aug. 25, 2022

Related U.S. Application Data

(60) Provisional application No. 63/148,391, filed on Feb. 11, 2021.

(51) Int. Cl.
*A61B 18/26*      (2006.01)
*A61B 18/20*      (2006.01)
(Continued)

(52) U.S. Cl.
CPC ............ *A61B 90/361* (2016.02); *A61B 18/20* (2013.01); *A61B 2017/00061* (2013.01);
(Continued)

(58) Field of Classification Search
CPC .................. A61B 90/361; A61B 18/20; A61B 2017/00061; A61B 2018/00577;
(Continued)

(56) References Cited

U.S. PATENT DOCUMENTS 5,042,980 A * 8/1991 Baker .................. A61B 18/245
                                                606/7
6,514,249 B1 * 2/2003 Maguire .................. A61N 7/02
                                                606/41

(Continued)

FOREIGN PATENT DOCUMENTS

EP            1544644 A1      6/2005

OTHER PUBLICATIONS

U.S. Appl. No. 63/120,793 (Year: 2020).*
(Continued)

*Primary Examiner* — Scott M. Getzow

(57)      ABSTRACT

A medical interventional tool has distal and proximal ends. A responsive material is located at the distal end or elsewhere along the interventional tool and is capable of providing a temperature-dependent or pressure-dependent optical response. At least one optical guide is in optical communication with the responsive material to collect an optical signal from the responsive material located at the distal end or other location along the interventional tool. The at least one optical guide further guides the collected optical signal to an optical output at the proximal end of the interventional tool. An optical response analyzer is configured to receive the collected optical signal from the optical output and to process the collected optical signal to derive therefrom a temperature or pressure reading or indication representative of a temperature or pressure at the distal end or other location along the interventional tool.

20 Claims, 8 Drawing Sheets

(51) Int. Cl.

| | | |
|---|---|---|
| *A61B 90/00* | (2016.01) | |
| *A61B 17/00* | (2006.01) | |
| *A61B 18/00* | (2006.01) | |

(52) U.S. Cl.
CPC ............... *A61B 2018/00577* (2013.01); *A61B 2018/00809* (2013.01); *A61B 2018/2005* (2013.01); *A61B 2090/064* (2016.02); *A61B 2090/3614* (2016.02)

(58) Field of Classification Search
CPC .. A61B 2018/00809; A61B 2018/2005; A61B 2090/064; A61B 2090/3614; A61B 2017/00057; A61B 2017/00066; A61B 2017/00084; A61B 2018/00434; A61B 2018/00446; A61B 2018/00982; A61B 2018/2244; A61B 2018/2261; A61B 2090/065; A61B 18/24; A61B 2018/2272
See application file for complete search history.

(56) References Cited

U.S. PATENT DOCUMENTS

| | | | |
|---|---|---|---|
| 2005/0075555 A1* | 4/2005 | Glukhovsky ............ | A61B 1/04 600/407 |
| 2008/0226217 A1* | 9/2008 | Kilic ...................... | G01H 9/004 385/12 |
| 2022/0175451 A1* | 6/2022 | Bukesov ................ | A61B 18/26 |

OTHER PUBLICATIONS

Boniello, et al: Dual-lifetime referencing (DLR): a powerful method for on-line measurement of internal pH in carrier-bound immobilized biocatalysts, BMC Biotechnology 2012, 12:11.
Ueno, et al: "An electro- and thermochromic hydrogel as a full-color indicator", Adv. Mater. 2007, 19, 2807-2812.
Bi, et al: "Real-Time Liquid Crystal pH Sensor for Monitoring Enzymatic Activities of Penicillinase", Adv. Funct. Mater. 2009, 19, 3760-3765.
Wang, et al: "Photonic Crystal Structures with Tunable Structure Color as Colorimetric Sensors", Sensors (Basel) Mar. 28, 2013;13(4):4192-213.
Seeboth, et al: "Piezochromic Polymer Materials Displaying Pressure Changes in Bar-Ranges", American Journal of Materials Science 2011, vol. 1, p. 139-134.
Sagara, et al: "Mechanically induced luminescence changes in molecular assemblies", Nature chemistry 2009, vol. 1, p. 605-610.
Teng et al: "Reversible Tuning Luminescent Color and Emission Intensity: A Dipeptide-Based Light-Emitting Material", Advanced Materials, vol. 24, Issue 9, Mar. 2, 2012.
Kabilan, et al: "Holographic glucose sensors", Biosensors and Bioelectronics 2005, vol. 20, p. 1602-1610,.
Sartain, et al: "Holographic Lactate Sensor", Anal. Chem. 2006, 78, 16, 5664-5670, ABSTRACT.
Mendes: "Stimuli-responsive surfaces for bio-applications", Chemical Society Reviews 2008, vol. 37, p. 2512-2529.
Lockwood, et al: "Self-assembly of amphiphiles, polymers and proteins at interfaces between thermotropic liquid crystals and aqueous phases", Surface Science Reports, vol. 63, Issue 6, p. 255-293 (2001).
Ganter, et al: "Continuous intravascular blood gas monitoring: development, current techniques, and clinical use of a commercial device", British Journal of Anaesthesia 2003, vol. 91, p. 397-407.

* cited by examiner

MEDICAL INTERVENTIONAL DEVICE HAVING OPTICAL TEMPERATURE OR PRESSURE SENSOR

This application claims the benefit of U.S. Provisional Application No. 63/148,391 filed Feb. 11, 2021, titled "LASER ABLATION SYSTEM HAVING OPTICAL TEMPERATURE SENSOR". This application is hereby incorporated by reference herein.

BACKGROUND

Laser ablation therapy involves targeted destruction of diseased tissue using a laser probe. The therapy is used to ablate tumors or blood clots, for example. As one example, laser ablation therapy may be performed in neurological procedures such as those performed on the brain and is usually performed under Magnetic Resonance Imaging (MRI) guidance. Laser interstitial thermal therapy (LITT) begin one example of such ablation therapy. In such cases laser ablation devices are positioned at precisely targeted areas in the brain to thereafter deliver laser ablation therapy at the targeted area. The MRI enables the surgeon to have a real time guidance of the position of the laser probe.

One desire is the ability to monitor temperature at the tissue near the laser probe before during and/or after the procedure in order to closely monitor progression of the ablation procedure.

In addition, pressure measurements are useful in diagnostic and therapeutic intervention in the cardiovascular system. There are multiple existing and potential applications for pressure sensing in cardiovascular procedures. For example, in coronary interventions, miniaturized pressure sensing, translated into the clinical parameter, FFR (Fractional Flow Reserve), is widely used. This procedure uses a miniature pressure sensing guide wire to measure pressure gradients across a stenosis in a coronary artery.

In another example, for structural heart interventions including catheter-based therapies of the aortic (TAVI), mitral (MitraClip), pulmonary (PPVI) and tricuspid valve, it is desirable to measure pressure across diseased and replaced heart valves to evaluate baseline and to assess the procedural success of such an intervention. Measurement is thus useful before, during and after the procedure.

In another example, for neurovascular embolization procedures, it is beneficial to monitor aneurysm pressure to assess rupture risk.

Today, pressure sensors developed for FFR are typically MEMS-based: either piezo-resistive or capacitive. MEMS-based sensors pose several disadvantages. For example, electrical cabling is needed to transfer signal from pressure wire tip to the proximal end. These cables increase mechanical stiffness of the guide wire, reducing their maneuverability, and increase the chance of dissection (perforating blood vessel wall).

Further miniaturization is limited by the size of the sensor chip and by electrical interconnects (such as bond pads) that connect the sensor to external power supply and provide data transfer. Increasing complexity in fabrication and assembly leads to higher manufacturing cost and requires more attention to robustness. The use of electrical wiring and powering also makes these devices vulnerable to electromagnetic (EM), radiofrequency (RF), and magnetic resonance (MR) interference. In addition, it is technologically challenging to integrate a large multitude of MEMS-based pressure sensors along a single interventional device, thus limiting the possibility of pressure profiling.

The following discloses solutions to these problems and others.

BRIEF SUMMARY

In some nonlimiting illustrative embodiments a medical device is disclosed, comprising: a medical interventional device configured for insertion into an associated subject to be treated; a temperature sensor comprising a responsive material capable of providing a temperature dependent optical response, the responsive material being arranged to respond to a temperature in the vicinity of at least a part of the medical interventional device; and at least one optical guide in optical communication with the responsive material to collect the optical signal and having an optical output connectable to an optical response analyzer configured to receive the collected optical signal and process the signal to derive therefrom a temperature reading or indication representative of the temperature.

In some nonlimiting illustrative embodiments a medical device is disclosed. An interventional tool, such as a catheter, guide wire, needle, or endoscope, has a distal end and a proximal end opposite from the distal end. A responsive material is located at the distal end of (or elsewhere along) the interventional tool and is capable of providing a temperature-dependent or pressure-dependent optical response. At least one optical guide is in optical communication with the responsive material to collect an optical signal from the responsive material located at the distal end of (or other location along) the interventional tool. The at least one optical guide further guides the collected optical signal to an optical output at the proximal end of the interventional tool. An optical response analyzer is configured to receive the collected optical signal from the optical output and to process the collected optical signal to derive therefrom a temperature or pressure reading or indication representative of a temperature or pressure at the distal end of (or other location along) the interventional tool.

In some nonlimiting illustrative embodiments a medical device is disclosed, comprising: an interventional tool (for example, a catheter, guide wire, needle, or endoscope) having a distal end and a proximal end opposite from the distal end; a responsive material located at the distal end of the interventional tool and capable of providing a pressure dependent optical response; at least one optical guide in optical communication with the responsive material to collect an optical signal from the responsive material located at the distal end of the interventional tool and guiding the collected optical signal to an optical output at the proximal end of the interventional tool; and an optical response analyzer configured to receive the collected optical signal from the optical output and to process the collected optical signal to derive therefrom a pressure reading or indication representative of a pressure at the distal end of the interventional tool.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION OF THE EMBODIMENTS

Figure 1:
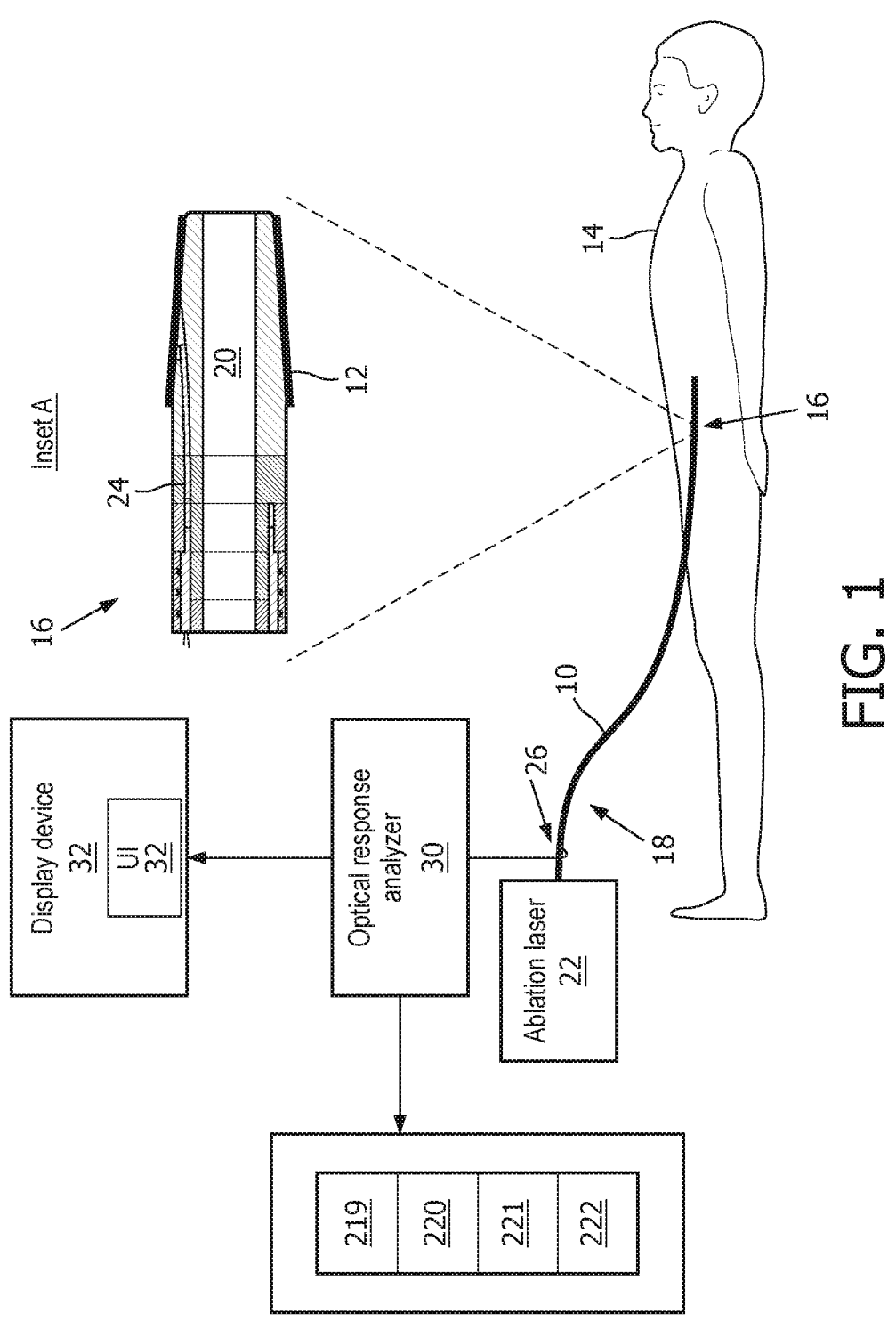
FIG. 1 diagrammatically shows a medical instrument in accordance with an aspect of the present disclosure.

In the following detailed description, for purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only and is not intended to be limiting. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only and is not intended to be limiting. As used in the specification and appended claims, the singular forms of terms 'a', 'an' and 'the' are intended to include both singular and plural forms, unless the context clearly dictates otherwise. Additionally, the terms "comprises", and/or "comprising," and/or similar terms when used in this specification, specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

In view of the foregoing, the present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

According to an aspect of the present disclosure, there is provided an interventional device, system including the device, and method, in which an optically responsive material is used that is capable of providing a temperature dependent optical response (or, in other embodiments, a pressure dependent optical response). The optical response may be sensed and transferred to a response analyzer to process the signal to extract a temperature (or pressure) corresponding to the response. Positioning such optically responsive material close to a part of the device with which a treatment is performed may then allow the use of the optical response of such material to be used to determine a temperature (or pressure) at or near a treatment site of the device.

An advantage of this approach is that no electronic circuit is needed. By using optical fibers for data and power transfer, intelligence is added to the interventional tools without sacrificing mechanical flexibility, safety, miniaturize-ability and MR compatibility. The device can be low-cost and robust, by minimizing the number of components and thus reducing fabrication and integration complexity. A range of responsive materials can be used to provide temperature, pressure, or other sensing capabilities. Smaller electrical cables (not used in some embodiments disclosed herein) have the further disadvantage that they are more lossy and suffer from relatively more electromagnetic interference.

Beside its sensing capabilities, an ideal sensor technology for interventional tools such as for example laser ablation tools for neurological treatment also should be miniaturized, robust, low-cost and low-power. Semiconductor-based sensors (such as for temperature) offer high potential in miniaturization. The capability of integration with integrated circuitry (IC) makes them particularly attractive where advanced sensing with large arrays is needed. On the other hand, increasing complexity in fabrication and assembly often leads to higher manufacturing cost and requires more attention to robustness. Another consideration is power and data transfer between the sensor (typically located at the tip of the interventional tool) and external units such as the optical analyzer. Most existing sensing technologies require electrical cables for data and power transfer. The electrical cable(s) need to be integrated into the interventional tool, therefore limiting its mechanical flexibility, miniaturization and MR compatibility.

This disclosure describes an advantageous use of a sensor device with a nonelectrical data transfer mechanism in an interventional device and system. The sensor includes an optically responsive material which provides an optical response dependent on temperature (or, in some other embodiments, pressure). An optically responsive material in this context can be a material that adapts one or more of its optical properties to a temperature in its environment. As a consequence, these materials can provide an optical response based on these optical properties that is, for example, temperature dependent. Changing properties may include one or more of: optical activity, refraction angle, characteristics, intensity, absorption transmission or emission (fluorescence or phosphorescence) either one in terms of color and/or intensity. Optical response characteristics that may change due to these changing material properties include for example radiation polarization, intensity or power, frequency spectrum or color, transmitted and/or reflected, although less preferred, emitted. Emission may be fluorescence or phosphorescence. The optical response signals may be transferred with optical fibers or other optical guides integrated in the interventional or surgical tools.

The optical response is then analyzed by an analyzer having (or operatively coupled with, in another view) an appropriate optical characteristics sensor, capable of sensing one or more of the aforementioned changing characteristics, and a processor (e.g., a microprocessor, microcontroller, or other electronic processor) for processing the signals sensed to extract a temperature reading. This may be done in real time or intermittently.

Readout of the optical response can also be done by naked eye, or by optical fibers, in which case a sensor capable of measuring the temperature dependent optical responses can be used that translates the response in electrical data to be processed by a controller of computer to extract the temperature.

The interventional device can be, for example, a catheter, a guide wire, a surgical tool, a needle, an endoscope, an implant, and so forth. The interventional device may also comprise an interventional tool for neurological treatments or brain surgery treatments.

The sensing responsive material can be any suitable material having a temperature (or, in other embodiments, pressure) dependent optical characteristic that may be read via an optical signal. Such examples of suitable materials can include electrochromic materials, electroluminescent materials, electrooptic materials, magneto-optic materials, photochromic materials, photoluminescent materials, photorefractive materials, thermochromic materials, thermoluminescent materials, mechanochromic materials, triboluminescent materials, photoelastic materials, chemochromic materials, chemoluminescent materials, and so forth.

In some examples, the stimulus can be temperature. In some examples, the optical response can be of either absorptive or emissive nature, such as a radiation frequency (i.e., color) change, a radiation intensity change, a radiation output type (e.g., continuous, pulsed, etc.), a radiation polarization change, a radiation propagation direction change (e.g., refraction, reflection, etc.), and so forth. The radiation can be, for example, infrared, near infrared, visible light, ultraviolet light, and so forth. The sensing responsive material can be, for example, inorganic, organic (such as for example liquid crystalline), mixtures and composites, polymers, composites, and so forth.

One class of optically responsive materials are liquid crystals. Liquid crystals exhibit one or more mesophases between the solid phase and the liquid phase. In these mesophases, the matter can flow like a liquid, but there is some directional order along one or multiple axes, like in a crystal. The type of order determines the properties, e.g. anisotropic optical properties.

One of the most common LC phases is the nematic phase. In this phase, rod-shaped molecules have long-range directional order with their long axes roughly parallel. In the specific case that the (nematic) liquid crystalline molecules are chiral molecules they may order in a chiral phase. A chiral nematic phase can also be obtained by the addition of a small amount of chiral dopant to achiral liquid crystals. In the chiral nematic liquid crystalline phase the chiral molecules induce a gradual rotation of the liquid crystalline director. The rotating director describes a helix with a certain pitch. The pitch is defined as the distance needed for a full rotation of the LC-director. Note that the structure repeats itself every half-pitch.

In general liquid crystals show a strong temperature dependence as the degree of order is strongly dependent upon temperature. Also chiral nematic liquid crystals show a strong change in pitch upon temperature differences. In general, a higher temperature will decrease the pitch, where a lower temperature will increase the pitch. The selectivity and range can be tuned by varying the liquid crystal molecules.

The helical structure is able to selectively reflect light of a narrow band of wavelengths proportional to the pitch length times the refractive index. A change in temperature alters in this way the wavelength of the reflected light. A higher temperature will give a blue-shift, where a lower temperature will give a red-shift. The color change is very fast, less than a second. This makes it possible to build a liquid crystal thermometer that displays the temperature of its environment by the reflected color. Combinations of various types of these liquid crystals are often used to create sensors with a wide variety of responses to temperature change. The thermochromic liquid crystals can be bought in solution or encapsulated in microcapsules via LCR Hallcrest (Glenview, IL, USA) and Gem'innov (Gemenos, France).

Optical temperature sensing can also be done by using thermochromic pigments or dyes. These compounds are easy to print and adhere well to textile. However, they typically show one color change upon temperature increase. This color change is difficult to manipulate, and the reverse reaction is rather slow (on the order of minutes).

Embodiments disclosed herein integrate responsive materials which have an optical response to a certain external stimulus at the tip of an interventional tool as a sensor. The signal (e.g. color change, a change in light emission, transmission, reflection or refraction) is collected by optical fiber(s) and transmitted to the proximal end for analysis.

Potential benefits of this sensing method include: 1. Simplicity (no electronic components in the catheter or other interventional device, no labor-intensive electronic assembly), therefore possible cost reduction, 2. Further miniaturization (no limitation by electrical cables or interconnects), 3. Mechanical flexibility, and 4. immunity to magnetic, electromagnetic (EM), and radio frequency (RF) fields such as may be generated in magnetic resonance (MR) imaging or other types of medical systems.

Furthermore, there is the possibility to integrate multi sensing modalities on the interventional device. This may lead to distributed sensing along the interventional devices shaft, sensing a variety of parameters with only one device, or a combination of both. The material provides many possibilities to designed variations. The following may be varied: size of silica particles, hardness of elastomeric film, and elasticity of elastomeric film. By changing these parameters, the pressure range and sensitivity of the material may be tuned toward the foreseen application. Other material candidates are a piezochromic material (such as dye doped polymers available from the University of Tokyo, Japan) and a piezochromic polymer material (available from the Fraunhofer Institute, Germany)

In some examples, the shape of the interventional medical device (e.g., a wire) can be obtained readily using the location of the passive ultrasound sensor. The shape can be quantified using the system that identifies the location of the passive ultrasound sensor. The location of the passive ultrasound sensor can be used to initialize image processing algorithms that use, for example, spatial filtering or cross correlation with a known shape, to determine the shape of the device. Once the shape of the interventional medical device is determined, a mesh of the interventional medical device can be generated and overlaid to enhance visualization.

With reference to FIG. 1, there is provided an interventional device 10, a medical device or system including the device 10, and a method, in which an optically responsive material 12 (see Inset A of FIG. 1) is used that is capable of providing a temperature dependent optical response (or, in other embodiments, a pressure dependent optical response). As seen in FIG. 1, the interventional tool 10 is configured (e.g., by construction as a suitably tubular tool such as a flexible catheter or guidewire, a probe, an endoscope, a rigid needle, a laser ablation tool, or the like) for insertion into a subject 14 such as a medical patient to be treated. The medical interventional device 10 is inserted into a blood vessel or other lumen of the subject 14 and manipulated by a surgeon or other medical professional to position the distal end 16 (shown in enlarged view in Inset A) of the interventional tool 10 at a target site in the subject 14. A proximal end 18 of the interventional device 10 remains outside the patient and may include various ports, inputs, controls, or so forth operable or usable by the surgeon to perform a medical procedure using the interventional device 10.

The illustrative interventional tool 10 is an ablation catheter 10 having an optical guide 20 running the length of the catheter 10 (the distal end of which is shown in Inset A) which delivers laser light from an ablation laser 22 (for example, an excimer laser of suitable optical power). At least one optical guide 20, such as an illustrative optical fiber 24, is in optical communication with the responsive material 12 to collect the optical signal. The optical fiber 24 can be configured to guide laser light from the ablation laser 22 to ablate target at the distal end 16 of the laser ablation tool 10. In this embodiment, the responsive material 12 comprises an annulus disposed around the optical fiber 24. In some embodiments, the optical fiber 24 includes a scattering or partially reflective structure configured to divert a portion of the laser light to the annulus of the responsive material 12 disposed around the optical fiber 24. The optical guide 24 has an optical output 26 that is connectable to an optical response analyzer 30 that is configured to receive the collected optical signal and process the signal to derive therefrom a temperature (or, in some embodiments, a pressure) reading or indication representative of the temperature (or pressure) of the optically responsive material 12 (and by inference, representative of the temperature of at least a part of the interventional tool 10 and or human tissue near the responsive material 12, such as at the distal end 16 of the interventional tool 10 in the illustrative example). In some examples, the responsive material 12 can be circumferentially or coaxially arranged around a longitudinal axis of the medical interventional device 10.

For example, the responsive material 12 can be arranged to provide a temperature dependent optical response that comprises one or more of the following temperature dependent characteristics: polarization, intensity or power, frequency spectrum or color. To do so, the responsive material 12 is arranged to provide an optical response based on an optical input signal that is changed by the responsive material based on absorption, scattering and/or reflection by the responsive material 12.

In some embodiments, the responsive material 12 comprises a chiral nematic liquid crystal material having a temperature dependent (or pressure dependent) pitch. In another example, the responsive material 12 comprises a photonic crystal material. In this example, the medical interventional device 10 further comprises a cavity (containing the photonic crystal material 12, and the cavity having a flexible cover layer configured to transfer pressure outside the cavity to the photonic crystal material 12.

In other embodiments, the optical response analyzer 30 may be configured to receive the collected optical signal and process the signal to derive therefrom a pressure reading or indication representative of the pressure of the optically responsive material 12 (and by inference, representative of the pressure at the distal end 16 of the interventional tool 10, for example the blood pressure in the case where the interventional tool 10 is inserted into the vascular system). Positioning the optically responsive material 12 close to a part of the device 10 with which a treatment is performed (typically the distal end 16 of the device 10) thus allows the use of the optical response of the responsive material 12 to be used to determine a temperature (or pressure) at or near a treatment site of the device.

While the illustrative interventional tool 10 is an ablation catheter, more generally the interventional tool may be a needle, catheter, guide wire, or so forth. The interventional tool is typically tubular so as to be inserted into a blood vessel or other tubular lumen of a human body (or, in the case of a biopsy needle or the like, to be inserted into the tissue itself), and in some embodiments (such as catheters or guide wires) is sufficiently flexible to enable a surgeon or other medical professional to guide the interventional tool 10 through a complex nonlinear lumen of the body of the subject 14, such a through blood vessels of the vasculature of the subject 14, to reach a target site. The optical fiber 20 carrying the ablation laser light in the illustrative ablation catheter 10 can be suitably replaced by other diagnostic and/or treatment apparatus depending on the type of interventional tool and the medical procedure to be performed. For example, the interventional tool could include one or more ultrasound transducer arrays for performing ultrasound imaging, ultrasonic treatment, or so forth, or may include a mechanical cutter for performing mechanical cutting of tissue, or so forth.

In the illustrative embodiment in which the interventional tool is the illustrative ablation catheter 10, the at least one optical guide 24 used to collect the optical signal from the responsive material 12 and transmit it to the optical response analyzer 30 is separate and distinct from the optical fiber 20 that carries the ablation laser light. However, in other contemplated embodiments a single optical fiber (which could be an optical fiber bundle or the like) may perform both functions, i.e. deliver the ablating laser light from the ablation laser 22 and also transmitting the optical signals from the responsive material 12 to the analyzer 30.

In another embodiment, the ablation laser source 22 can be replaced with an optical signal source 22 arranged to provide a source optical signal to the responsive material 12 such that the optical response is also based on the source optical signal.

In another embodiment, the optical analyzer 30 includes a display device 32 configured to display a user interface 34 for providing the indication of temperature or pressure to a user.

In laser ablation catheter embodiments in which the ablation laser light is applied to the responsive material 12 to generate the temperature (or pressure) dependent response, it may be beneficial to ensure the ablation laser light striking the responsive material 12 is of sufficiently low intensity to avoid damaging the responsive material 12 (or, in the case of a temperature sensor, artificially heating the responsive material). In some embodiments, this is achieved by having the responsive material 12 as a thermochromic material on the inside near the distal end 16 of the catheter 10 and moving the fiber 24 such that it is outside the catheter 10 (i.e. the catheter 10 is not obstructing the light coming out of the fiber 24 during ablation but partly (when retracted)) during measurement of temperature.

In another example, an end of the optical fiber 24 can be covered with a transparent material with a certain thickness and provide the responsive material 12 as thermochromic material in an annulus on top of the transparent material. The exit beam of the fiber 24 will diverge. The central part of this diverging beam will traverse the central opening of the annulus where there is no thermochromic material and will not be hindered by it and is used to ablate the tissue. The outer part of the beam (which has lower intensity) will hit the annulus and will reflect light back to the core for measuring the temperature. Since the light hitting the thermochromic material will have lower intensity than the central part of the beam that performs the ablation, the light hitting the thermochromic material will not damage the material. In a further embodiment the above fiber cover can be made to have a central transparent part and a diffusing annulus part. Hence the central part of the beam is not affected while the outer part is scattering and diffusing the outer part of the beam such that the light intensity before hitting the thermochromo material is even lower. The scattering material will furthermore help increase the light that is scattered back from the thermochromo material to the core of the fiber and guided to back to the detector for measuring the temperature.

In another example, a top of the optical fiber 24 can include using a material at the tip thereof with a wavelength related refraction index, which could direct the beam in one direction if it is the ablation beam, and in another if it is the temperature measurement beam.

In another example, the optical fiber 24 can move within the medical instrument 10. For example, when the medical instrument 10 comprises an ablation catheter, the optical fiber 24 can extend out of the catheter, and then be retracted for a temperature (or pressure) measurement with walls of the transparent catheter 10 embedding the thermochromatic material 12. To have the measurement beam go sideways, we could imagine a diaphragm at the end of catheter 10 which would act as a diffuser (e.g. transparent rubber type) which naturally closes when the fiber 24 is retracted in the catheter 24.

Figure 8:
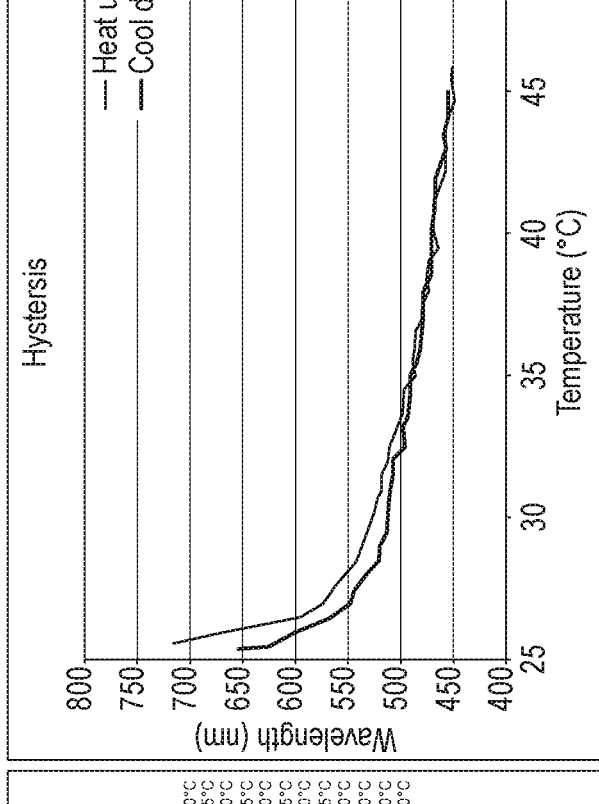
FIG. 8 shows data for a suitable temperature-dependent material suitably used in the temperature sensor of some medical instruments or devices disclosed herein.
Figure 8:
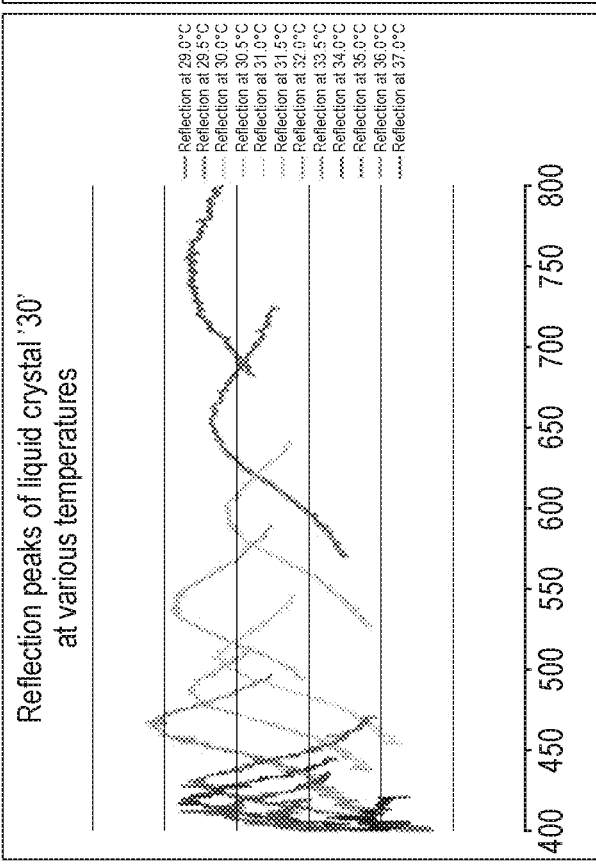

In one example for temperature sensing, the optically responsive material 12 may comprise a thermometer strip with 16 liquid crystals, each reactive to a different temperature is used. The liquid crystal that reacts thus indicates the current local temperature. In some bench tests of such a thermometer strip, the color change of the liquid crystal responsive to 30° C. on the thermometer strip was analyzed on the photonic needle test setup. The liquid crystal was analyzed at 26-37° C. to plot the color change. The result is shown in FIG. 8, lefthand plot. The color of the liquid crystal temperature sensor was observed to change very fast in reaction to temperature change. The reflected color can be analyzed with the photonic needle test setup.

Also used was liquid crystal SPN100/R25C5 W via LCR Hallcrest. This contains liquid crystals encapsulated in microcapsules. When applied to a (black) surface colder than 25° C., the layer is transparent. Upon heating from 25° C. to 30° C., the reflected color will change from red to blue. The blue color is visible until 40° C., at higher temperatures the layer is again transparent. The temperature response and hysteresis are analyzed on the photonic needle test setup, see FIG. 8, righthand plot. The hysteresis is rather large, 1.5° C. It is expected that this can be optimized by an improved measurement method, and suitable selection of the substrate and liquid crystal optimization.

The thermochromic liquid crystal SPN100/R25C5 W of LCR Hallcrest was applied to black cotton textile. This resulted in thermochromic textile. The liquid crystals do not adhere well to the textile, they are washed off easily. It was found that the layer thickness must be controlled in order to get a repeatable result.

In another embodiment, an arrangement similar to a 'bar code' structure can be used, where each bar reacts to a different temperature. Each temperature has in that case a specific bar code signature.

Figure 2:
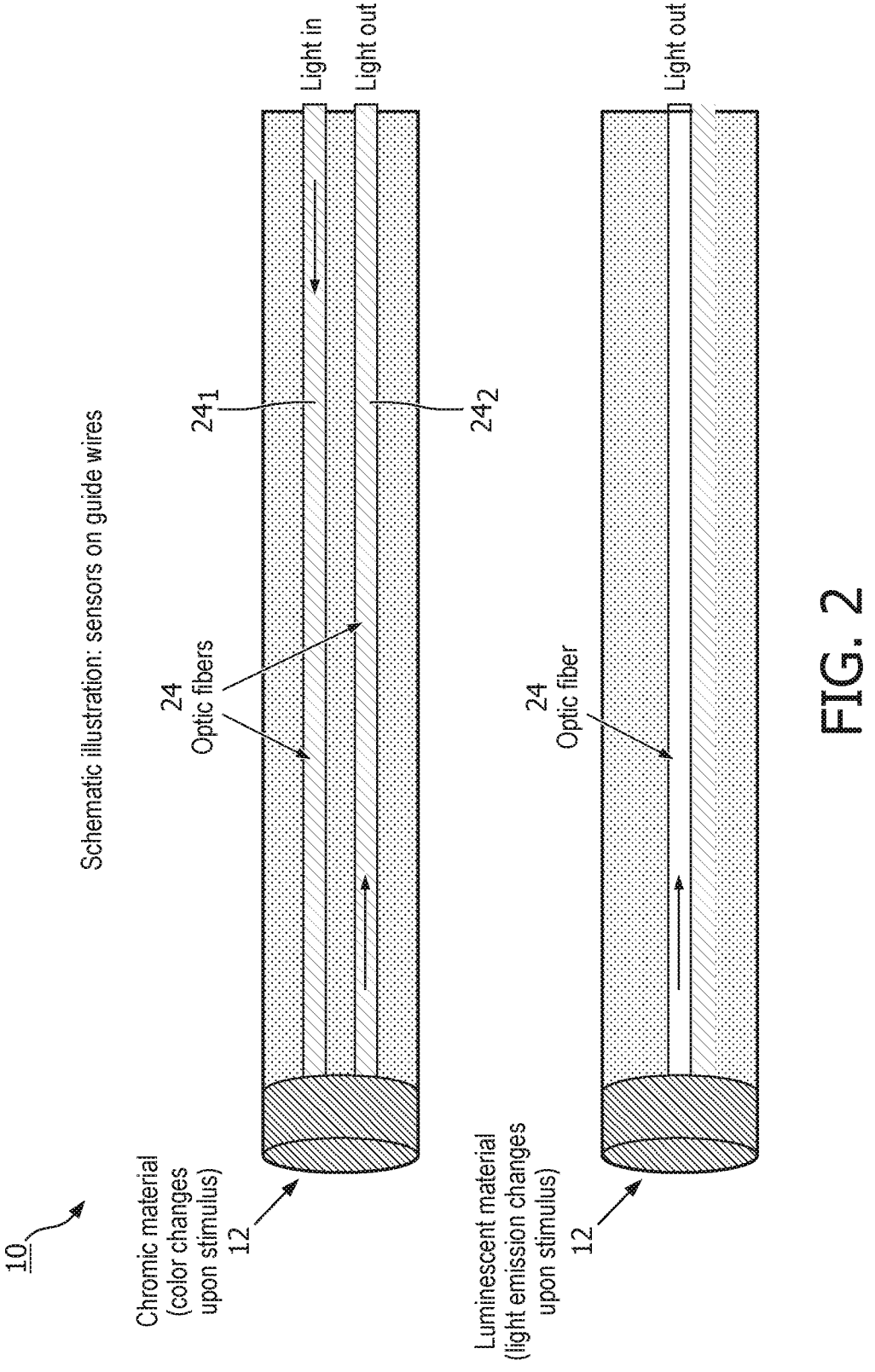
FIGS. 2-7 show alternative embodiments of the instrument of FIG. 1.
Figure 3:
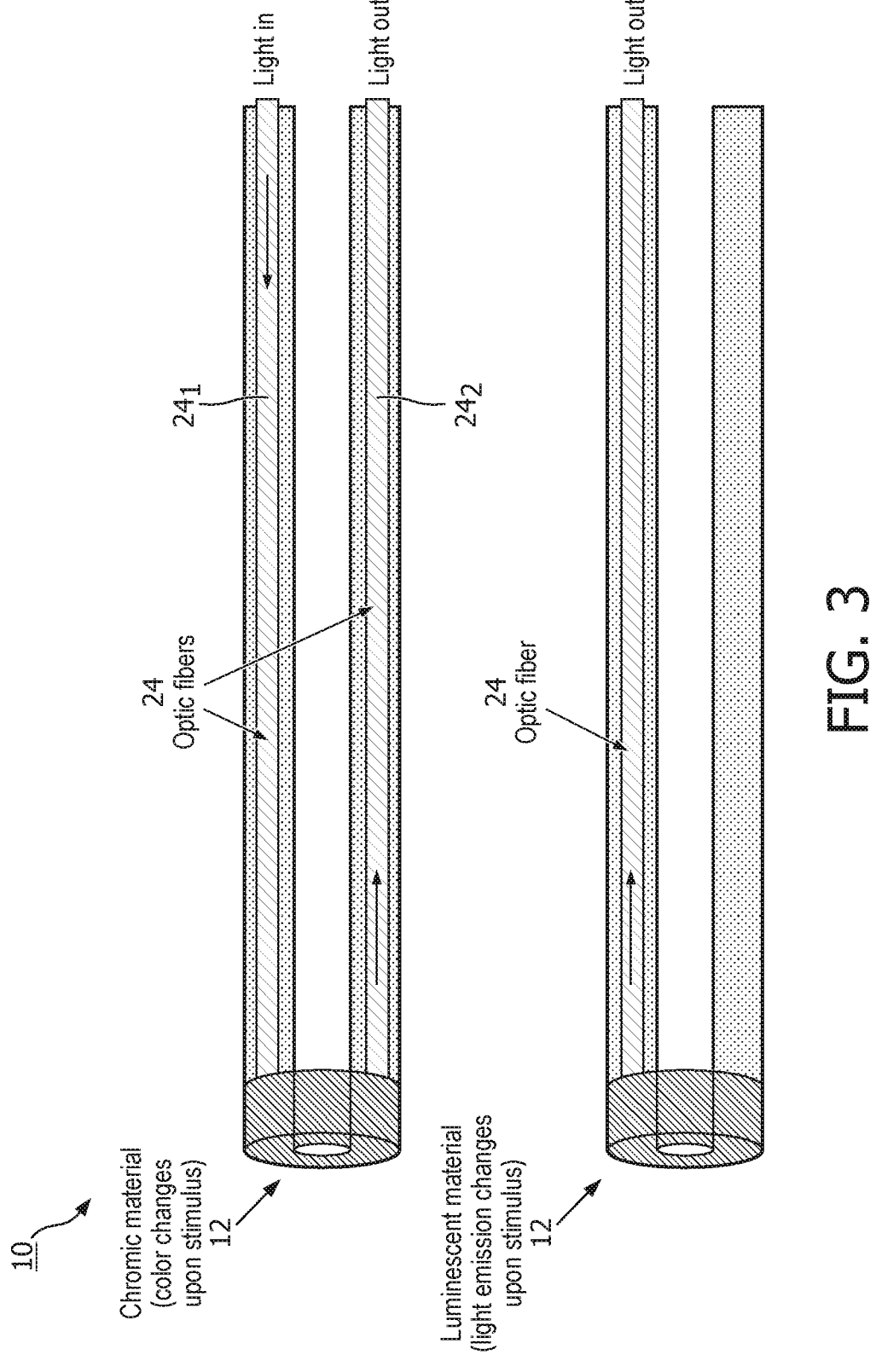

With reference to FIGS. 2 and 3, respective top drawings, for embodiments in which the responsive material 12 is a chromatic material which changes color upon stimulus, two optical fibers can be used: one optical fiber $24_1$ to deliver a broadband light from the external light source to the responsive material 12; and a second optical fiber $24_2$ to collect the reflected/scattered light from the responsive material 12 and transmit it to the external optical response analyzer 30 for analysis. FIG. 2 shows an embodiment in which the responsive material 12 forms an endcap at the distal end 16 of the of the medical interventional device 10, while FIG. 3 shows an embodiment in which the responsive material 12 forms an annulus around the distal end 16 of the medical interventional device 10. The latter arrangement of FIG. 3 advantageously provide an open central annulus for use in other operations such as laser ablation, carrying a cutting tool, carrying an ultrasound transducer array, or so forth.

With reference to FIGS. 2 and 3, respective bottom drawings, for embodiments in which the responsive material 12 is a luminescent material which changes emission upon stimulus, only one optical fiber 24 is sufficient to collect the emitted light. Again, FIG. 2 shows an embodiment in which the responsive material 12 forms an endcap at the distal end 16 of the of the medical interventional device 10, while FIG. 3 shows an embodiment in which the responsive material 12 forms an annulus around the distal end 16 of the medical interventional device 10.

Figure 4:
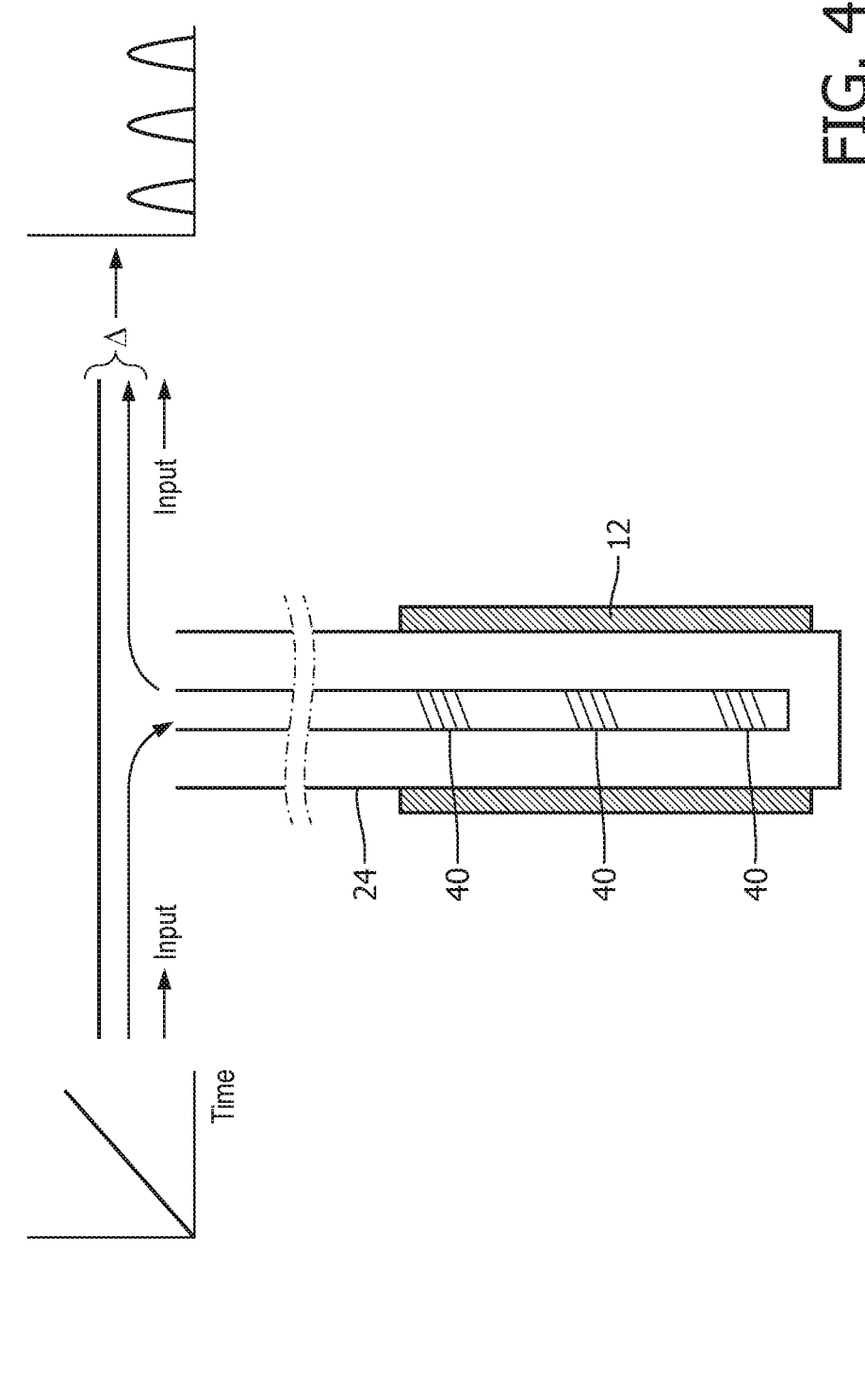

With reference to FIG. 4, in an alternative embodiment, the input light and output light can be transmitted over the same fiber, for example by using a dichroic mirror, beam splitter, lens, optical filter, grating, polarizer, or wave plate or any combination of these at the proximal end 18 of the device 10, or at the distal end 16 of the device 10, or elsewhere along the device 10. For example, FIG. 4 illustrates use of slanted Bragg gratings 40 for this purpose. The input light is guided towards the responsive material 12 cladding the fiber 12 by slanted Bragg gratings 40. Only a part of the light is reflected, so most of the light will travel to the next slanted Bragg grating. A part of the wavelength spectrum of the light will reflect on the responsive material 12 (depending on the temperature for a temperature sensor, or on the pressure for a pressure sensor) and is reflected back to the proximal end 18 of the catheter for further analysis. When a modulated light source is used, pathlength differences may be detected and the place of the measured pressure may be deducted.

Figure 5:
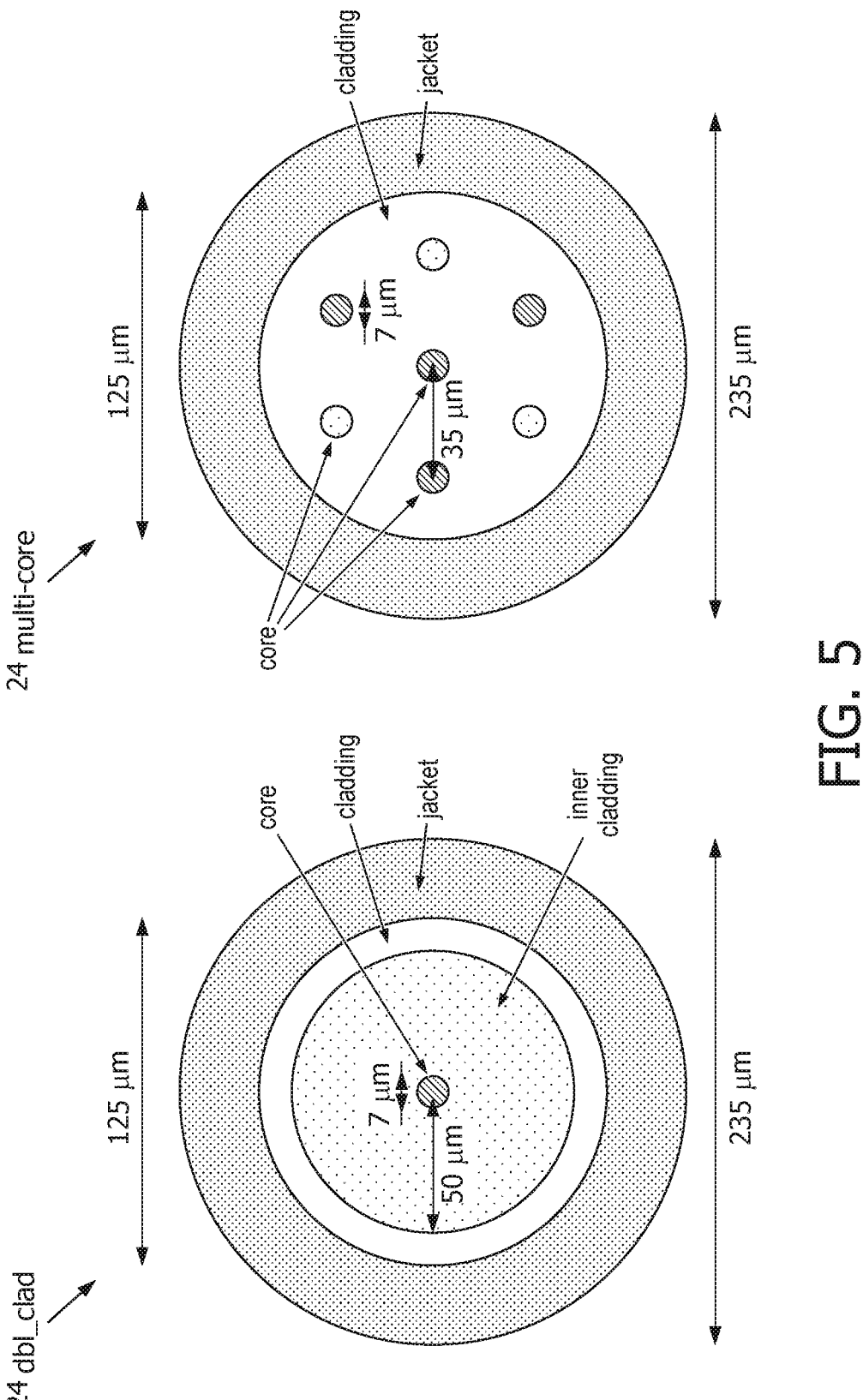

With reference to FIG. 5, in some embodiments the input light and output light may be transmitted over a special type of optical fiber, such as a double cladding optical fiber $24_{dbl\_clad}$ or multi-core optical fiber $24_{multi\_core}$. This may provide different illumination and collection angles or patterns at the distal end. This can be beneficial, for example, when laser light is used as input, and which may be transmitted over a single mode core at the center of a dual cladding optical fiber. A diffuse light response from the tip may be collected with a large numerical aperture and core diameter, formed between the inner and outer cladding of the dual cladding optical fiber.

For guide wires, the optical fiber(s) can be integrated in the guide wire body. For catheters and needles, the optical fiber(s) can be integrated in the wall and leave the lumen open.

In general, the sensing responsive material can be positioned at the very tip of the distal end 16 of the device 10, or on the sidewall of the device.

In general, there can be sensing responsive material at one, or more than one location of the device.

In further contemplated variants, there can be one, or more than one type of sensing responsive material on the device.

In further contemplated variants, the stimulus can be converted into optical signal either directly by one material, or in multiple steps by a combination of different materials.

In some embodiments, the temperature responsive material 12 may be coated onto an end of the optical fiber 24, and to protect the temperature responsive material 12 the fiber on which the material 12 is applied can be encapsulated by a one end close quartz tubing.

Figure 6:
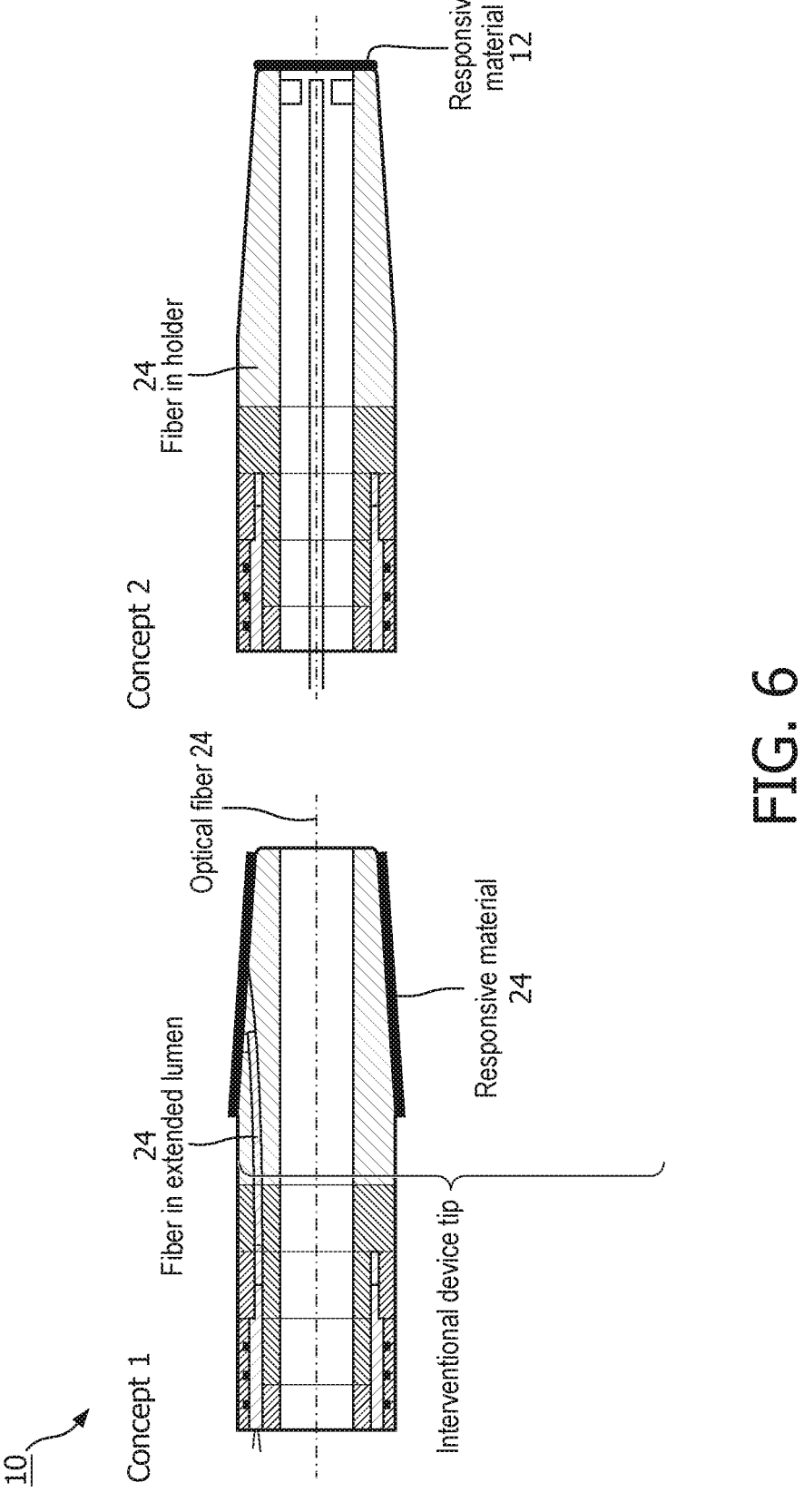

It will be appreciated that structural embodiments such as those of FIGS. 2-5 can also be used for pressure sensors. In general, the temperature- or pressure-responsive material With reference to FIG. 6, another illustrative embodiment is shown, in which a pressure sensing responsive material 12 is positioned at the very tip of the device 10 (righthand drawing of FIG. 6), or on the sidewall of the device (lefthand drawing of FIG. 6). The responsive material 12 can be located at one (single point), or more than one location of the device (multi point or distributed). There can be one, or more than one type of sensing responsive material on the device (e.g., both temperature and pressure).

The stimulus can be converted into optical signal either directly by one material, or in multiple steps by a combination of different materials.

In the following, an example of a pressure-sensitive sensor embodiment is described. This embodiment is based on the use of a structured photonic crystal material developed by Opalux (available from Opalux Inc., Toronto, Ontario, Canada). In this photonic crystal material, the Bragg reflection of a specific wavelength changes as result of periodic modulation of refractive index in the regular structured elastomeric material. This results in a highly adjustable materials platform. The response can be tuned in a wide range (including color range, pressure range, response time, hysteresis, etc). Sensitivities up to ~0.5 nm shift/mm Hg are feasible, enough for in body pressure sensing.

Another photonic crystal material suitable for use in the pressure sensor was tested as follows. Commercially available monodisperse non-porous silica nanoparticles with particle sizes in the range from 100-1000 nm were allowed to self-assemble into a colloidal photonic crystal structure by solvent evaporation induced self-assembly on a flat glass or silicon substrate. After complete evaporation of the solvent, the resulting colloidal photonic crystal structure was exposed to tetramethoxysilane vapor in vacuum to crosslink the silica particles. The substrate with the crosslinked colloidal photonic crystal was placed in a petri-dish and a mixture of 2-ethylhexyl methacylate (89%), ethylene glycol dimethacrylate crosslinker (10%) and Irgacure 651 (1%) was carefully poured on top of the colloidal photonic crystal until complete submergion. Thereafter, the Petri dish was transferred to a nitrogen purged box with a glass cover lid. The sample was exposed to 365 nm UV light with an intensity of 1 mW/cm2 for 30 minutes. The photopolymerization yields a nanoparticle filled elastomeric film.

After methacrylate conversion of >70% is reached the nitrogen purged box is opened and the excess top layer of the elastomer is slowly peeled off from the surface of the colloidal photonic crystal structure. Subsequently, the resulting polymer-silica composite film was cut into the desired size and shape and transferred to a 2% aqueous solution of hydrogen fluoride in order to dissolve the silica particles. After 5-20 minutes, the polymer elastomeric films comes floating of the substrate to the surface and is transferred to distilled water where it floats on top. Finally the film is transferred to a flexible plastic substrate and dried under nitrogen flow. The plastic substrate was chosen to have a refractive index as close as possible to the refractive index of the optical fibers in the minimally invasive device.

Figure 7:
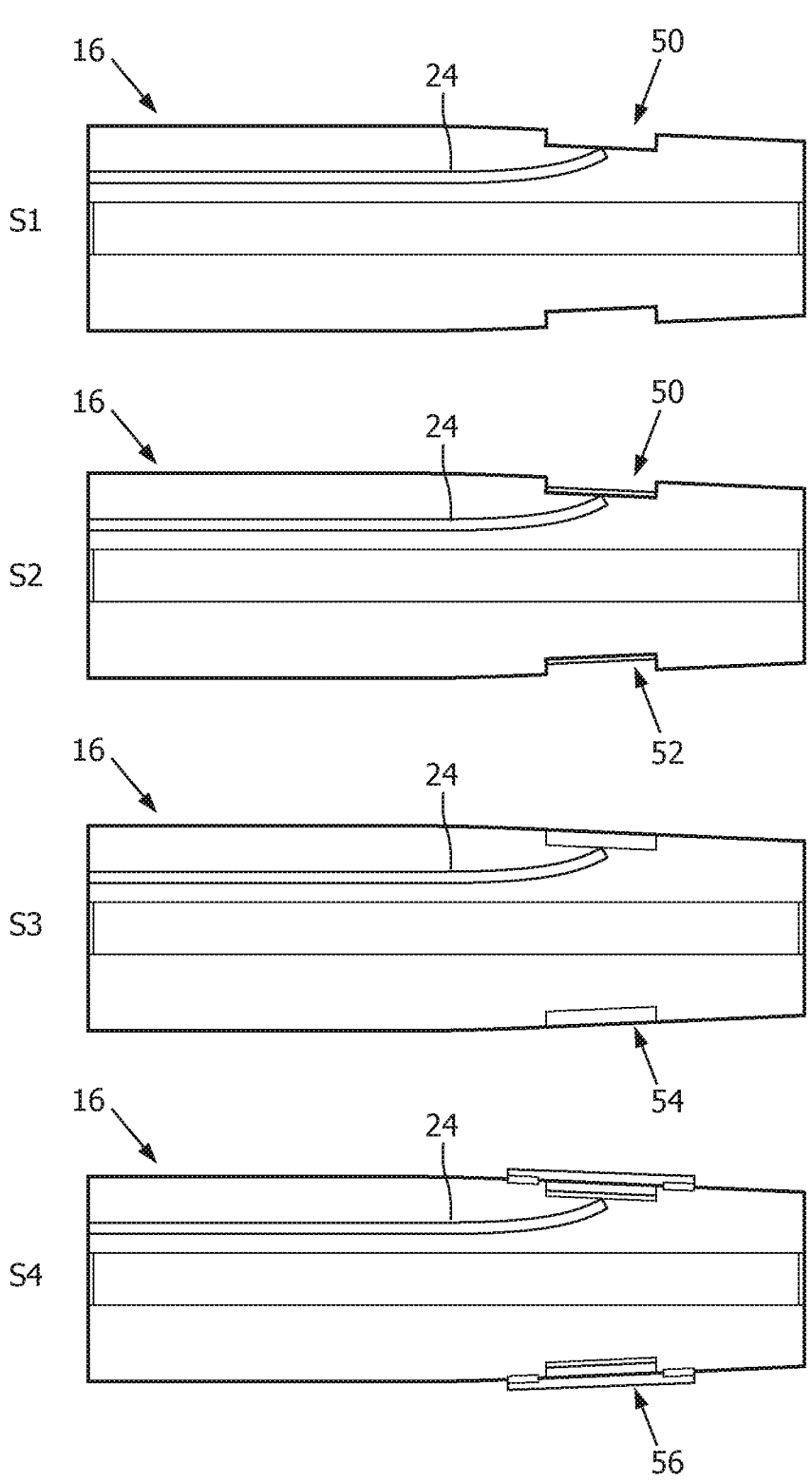

As shown in FIG. 7, the elastomeric photonic structure film for use in pressure sensing may be integrated with a medical interventional device 10 in the following manner. In a step S1, the distal end 16 of the medical interventional device 10 (or other location along the device 10 where pressure is to be sensed) is equipped with a sleeve 50 close to the tip of the device, exposing the tip of the optical fiber 24. In a step S2, a refractive index matching glue 52 is dispensed in this sleeve 50. In a subsequent step S3, an elastomeric polymer photonic structure film 54 (for example, an Opalux photonic crystal material, or a photonic crystal formed from monodisperse non-porous silica nanoparticles as previously described) is glued in the sleeve 50. In a step S4, a thin flexible plastic cover layer 56 is placed over the sleeve 50. In use, variations in (for example) blood pressure will push against the thin flexible cover layer 56 and deform the elastomeric polymer photonic structure film 54. The resulting deformation of the photonic structure 54 and its lattice spacing, will induce a shift in the spectral position and bandwidth of the reflected light that is delivered to the pressure sensing material by the optical fiber 24. The reflected light is transported back to the detector by the same optical fiber 24. Changes in the spectrum of the reflected light are finally translated into changes in blood pressure by the optical response analyzer 30 of FIG. 1.

Referring back to FIG. 1, the analyzer 30 includes an optical sensor for example a camera or light intensity sensor 219 and a controller 220 and memory 221 that stores instructions and a processor 222 that executes the instructions. It is noted that the controller 220 as described herein may be distributed among multiple devices that each include a combination of memory and processor to perform one or more characteristic functions attributed to the controller 220 herein.

Upon receipt of an optical response by the sensor 219, the sensor transforms the response in a representative electrical signal that is preferably digitized into response data that may be processed by the processor 222 once received or obtained by the processor 222.

The analyzer 30 can have an output where it provides data representative of a temperature reading or indication derived by the processor 222 from the response data. A suitable user interface 34 may be communicatively connected to the analyzer 30 for providing the reading or indication to a user such as a patient or physician.

A processor 222 for a controller is tangible and non-transitory. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A processor is an article of manufacture and/or a machine component. A processor 222 for a controller 220 is configured to execute software instructions to perform functions as described in the various embodiments herein. A processor 222 for a controller 220 may be a general-purpose processor or may be part of an application specific integrated circuit (ASIC). A processor 222 for a controller may also be a microprocessor, a microcomputer, a processor chip, a controller, a microcontroller, a digital signal processor (DSP), a state machine, or a programmable logic device. A processor 222 for a controller may also be a logical circuit, including a programmable gate array (PGA) such as a field programmable gate array (FPGA), or another type of circuit that includes discrete gate and/or transistor logic. A processor 222 for a controller may be a central processing unit (CPU), a graphics processing unit (GPU), or both. Additionally, any processor described herein may include multiple processors, parallel processors, or both. Multiple processors may be included in, or coupled to, a single device or multiple devices. A "processor" as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each including a processor or processors. Many programs have instructions performed by multiple processors that may be within the same computing device or which may even be distributed across multiple computing devices.

Memories such as the memory 221 described herein are tangible storage mediums that can store data and executable instructions and are non-transitory during the time instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A memory described herein is an article of manufacture and/or machine component. Memories described herein are computer-readable mediums from which data and executable instructions can be read by a computer. Memories as described herein may be random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, Blu-ray disk, or any other form of storage medium known in the art. Memories may be volatile or non-volatile, secure and/or encrypted, unsecure and/or unencrypted. "Memory" is an example of a computer-readable storage medium. Computer memory is any memory which is directly accessible to a processor. Examples of computer memory include, but are not limited to RAM memory, registers, and register files. References to "computer memory" or "memory" should be interpreted as possibly being multiple memories. The memory may for instance be multiple memories within the same computer system. The memory may also be multiple memories distributed amongst multiple computer systems or computing devices.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A medical device, comprising:
   a medical interventional device configured for insertion into an associated subject to be treated;
   a temperature sensor comprising a chromatic material capable of providing a temperature dependent optical response, the chromatic material being disposed on or proximal to a distal end of the medical interventional device and arranged to respond to a temperature in the vicinity of at least a part of the medical interventional device; and
   at least one optical guide in optical communication with the chromatic material to collect the optical signal and having an optical output connectable to an optical response analyzer configured to receive the collected optical signal and process the signal to derive therefrom a temperature reading or indication representative of the temperature, wherein the at least one optical guide has a distal end and the chromatic material having a proximal side that is disposed distally of the distal end of the at least one optical guide, the at least one optical guide further comprising:
   a first optical fiber configured to deliver light to the chromatic material; and
   a second optical fiber configured to collect reflected light from the chromatic material.

2. The medical device as claimed in claim 1, wherein the chromatic material is arranged to provide a temperature dependent optical response that comprises one or more of the following temperature dependent characteristics: polarization, intensity or power, frequency spectrum or color.

3. The medical device as claimed in claim 1, wherein the medical interventional device comprises a needle, probe or catheter.

4. The medical device as claimed in claim 1, wherein the chromatic material is arranged to provide an optical response based on an optical input signal that is changed by the chromatic material based on absorption, scattering and/or reflection by the chromatic material.

5. The medical device as claimed in claim 1, wherein the chromatic material is circumferentially or coaxially arranged around a longitudinal axis of the medical interventional device.

6. A medical device, comprising:
   an interventional tool having a distal end and a proximal end opposite from the distal end;
   a chromatic material located on or proximal to the distal end of the interventional tool and capable of providing a temperature dependent or pressure dependent optical response;

at least one optical guide in optical communication with the chromatic material to collect an optical signal from the chromatic material located at the distal end of the interventional tool and guiding the collected optical signal to an optical output at the proximal end of the interventional tool, wherein the at least one optical guide includes a distal end and the chromatic material is disposed at the distal end of the at least one optical guide, the at least one optical guide further comprising:
a first optical fiber configured to deliver light to the chromatic material; and
a second optical fiber configured to collect reflected light from the chromatic material, the first and second optical fibers each having distal ends disposed proximally to the chromatic material; and
an optical response analyzer configured to receive the collected optical signal from the optical output and to process the collected optical signal to derive therefrom a temperature or pressure reading or indication representative of a temperature or pressure at the distal end of the interventional tool.

7. The medical device as claimed in claim 6, wherein:
the interventional tool comprises a laser ablation tool;
the at least one optical guide comprises an optical fiber configured to guide laser light to ablate target at the distal end of the laser ablation tool; and
the chromatic material comprises an annulus disposed around the optical fiber.

8. The medical device as claimed in claim 7, wherein the optical fiber includes a scattering or partially reflective structure configured to divert a portion of the laser light to the annulus of the chromatic material disposed around the optical fiber.

9. The medical device as claimed in claim 6, wherein the chromatic material is capable of providing a temperature dependent optical response.

10. The medical device as claimed in claim 9, wherein the chromatic material comprises a chiral nematic liquid crystal material having a temperature dependent pitch.

11. The medical device as claimed in claim 6, wherein the chromatic material is capable of providing a pressure dependent optical response.

12. The medical device as claimed in claim 11, wherein:
the chromatic material comprises a photonic crystal material; and
the medical interventional device further comprises a cavity containing the photonic crystal material, the cavity having a flexible cover layer configured to transfer pressure outside the cavity to the photonic crystal material.

13. The medical device as claimed in claim 6, wherein the optical analyzer further includes a display device configured to display a user interface for providing the indication of temperature or pressure to a user.

14. The medical device as claimed in claim 6, further comprising an optical signal source arranged to provide a source optical signal to the chromatic material such that the optical response is also based on the source optical signal.

15. A medical device, comprising:
an interventional tool having a distal end and a proximal end opposite from the distal end;
a chromatic material located on or proximal to the distal end of the interventional tool and capable of providing a pressure dependent optical response;
at least one optical guide in optical communication with the chromatic material to collect an optical signal from the chromatic material located at the distal end of the interventional tool and guiding the collected optical signal to an optical output at the proximal end of the interventional tool, wherein the at least one optical guide includes a distal end and the chromatic material is disposed at the distal end of the at least one optical guide, the at least one optical guide further comprising:
a first optical fiber configured to deliver light to the chromatic material; and
a second optical fiber configured to collect reflected light from the chromatic material; and
an optical response analyzer configured to receive the collected optical signal from the optical output and to process the collected optical signal to derive therefrom a pressure reading or indication representative of a pressure at the distal end of the interventional tool.

16. The medical device as claimed in claim 15, wherein:
the interventional tool comprises a laser ablation tool;
the at least one optical guide comprises an optical fiber configured to guide laser light to ablate target at the distal end of the laser ablation tool; and
the chromatic material comprises an annulus disposed around the optical fiber.

17. The medical device as claimed in claim 16, wherein the optical fiber includes a scattering or partially reflective structure configured to divert a portion of the laser light to the annulus of the chromatic material disposed around the optical fiber.

18. The medical device as claimed in claim 15, wherein the chromatic material is capable of providing a pressure dependent optical response.

19. The medical device as claimed in claim 18, wherein:
the chromatic material comprises a photonic crystal material; and
the medical interventional device further comprises a cavity containing the photonic crystal material, the cavity having a flexible cover layer configured to transfer pressure outside the cavity to the photonic crystal material.

20. The medical device as claimed in claim 15, wherein the optical analyzer further includes a display device configured to display a user interface for providing the indication of temperature or pressure to a user.

* * * * *